(12) United States Patent
Berger et al.

(10) Patent No.: US 10,499,883 B2
(45) Date of Patent: Dec. 10, 2019

(54) METHODS AND SYSTEMS FOR SPATIAL COLOR FLOW FOR DIAGNOSTIC MEDICAL IMAGING

(71) Applicant: General Electric Company, Schenectady, NY (US)

(72) Inventors: Josef Berger, Zipf (AT); Christian Perrey, Zipf (AT)

(73) Assignee: General Electric Company, Schenectady, NY (US)

(*) Notice: Subject to any disclaimer, the term of this patent is extended or adjusted under 35 U.S.C. 154(b) by 336 days.

(21) Appl. No.: 15/436,084

(22) Filed: Feb. 17, 2017

(65) Prior Publication Data

US 2018/0235578 A1 Aug. 23, 2018

(51) Int. Cl.
*A61B 8/08* (2006.01)
*A61B 8/06* (2006.01)
*A61B 8/00* (2006.01)

(52) U.S. Cl.
CPC .............. *A61B 8/5207* (2013.01); *A61B 8/06* (2013.01); *A61B 8/5246* (2013.01); *A61B 8/4483* (2013.01); *A61B 8/465* (2013.01); *A61B 8/488* (2013.01)

(58) Field of Classification Search
CPC ......... A61B 8/06; A61B 8/065; A61B 8/5207; A61B 8/5215; A61B 8/5233; A61B 8/14; A61B 8/485; A61B 8/488; A61B 8/463; A61B 8/465; A61B 8/5246–5261; G01S 15/8984
See application file for complete search history.

(56) References Cited

U.S. PATENT DOCUMENTS

| | | | |
|---|---|---|---|
| 6,511,426 B1* | 1/2003 | Hossack | G01S 15/899 600/437 |
| 9,538,982 B2* | 1/2017 | Anthony | A61B 8/13 |
| 2004/0019278 A1* | 1/2004 | Abend | G01S 7/52026 600/454 |
| 2004/0220474 A1* | 11/2004 | Abend | G01S 7/52026 600/437 |
| 2004/0267127 A1* | 12/2004 | Abend | A61B 8/06 600/450 |
| 2005/0004461 A1* | 1/2005 | Abend | G01S 7/52026 600/437 |
| 2006/0253031 A1 | 11/2006 | Altmann et al. | |

(Continued)

*Primary Examiner* — Angela M Hoffa
*Assistant Examiner* — Virag B Patel
(74) *Attorney, Agent, or Firm* — Dean D. Small; The Small Patent Law Group, LLC

(57) ABSTRACT

The systems and methods described herein relate to providing spatial color flow imaging for diagnostic medical imaging. The systems and methods acquire ultrasound data along a first two-dimensional (2D) plane and at least a second 2D plane from a matrix array probe for a region of interest (ROI), calculate a first flow velocity based on the ultrasound data along the first 2D plane, calculate a second flow velocity based on the ultrasound data along the second 2D plane, and generate a first color flow image based on the first flow velocity. The systems and methods further generate a second color flow image based on the second flow velocity, generate an anatomical image based on the ultrasound data on a display, and overlay the first and second color flow images to the anatomical image.

20 Claims, 10 Drawing Sheets

(56) References Cited

U.S. PATENT DOCUMENTS

| | | | |
|---|---|---|---|
| 2010/0222680 A1* | 9/2010 | Hamada | A61B 8/06 600/443 |
| 2011/0196237 A1* | 8/2011 | Pelissier | A61B 8/06 600/454 |
| 2016/0000408 A1* | 1/2016 | Matsunaga | A61B 8/06 600/441 |
| 2016/0015366 A1* | 1/2016 | Haugaard | A61B 8/06 600/441 |
| 2016/0174931 A1* | 6/2016 | Pelissier | A61B 8/06 600/454 |
| 2016/0361040 A1* | 12/2016 | Tanaka | A61B 8/06 |
| 2018/0125460 A1* | 5/2018 | Perrey | A61B 8/13 |

* cited by examiner

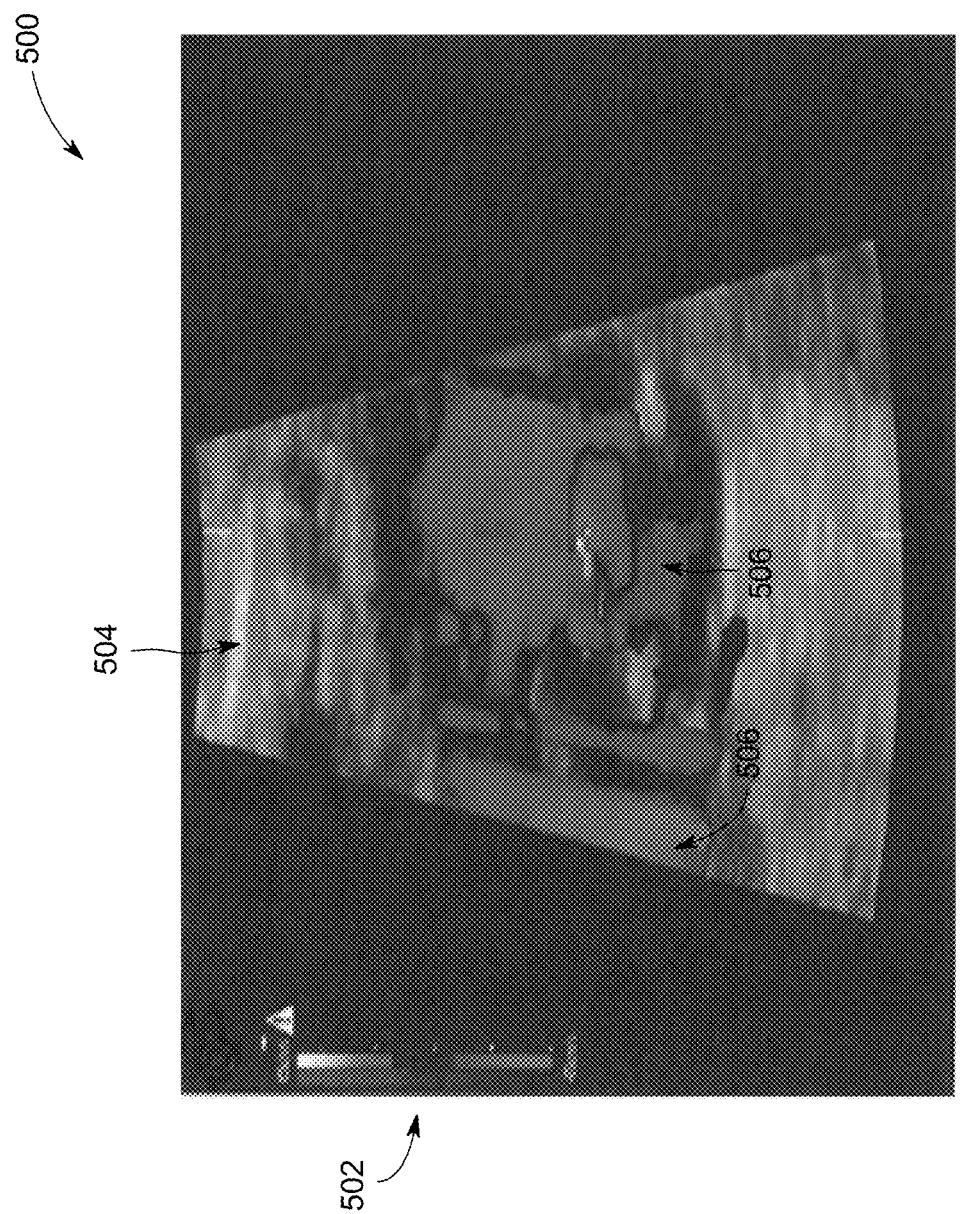

METHODS AND SYSTEMS FOR SPATIAL COLOR FLOW FOR DIAGNOSTIC MEDICAL IMAGING

FIELD

Embodiments described herein generally relate to providing spatial color flow imaging for diagnostic medical imaging based on ultrasound data acquired along azimuth and elevation planes.

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation to perform the different scans. The signals received at the probe are then communicated and processed at a back end. When the scan is complete, the ultrasound data may be stored on a patient archive communication system (PACS) for retrospective examination.

Conventional ultrasound imaging systems include a set of imaging modes, such as B-mode, color flow, and spectral Doppler imaging. In the B-mode, such ultrasound imaging systems create two or three dimensional images of tissue structure in which the brightness of a pixel is based on the intensity of the echo return. For color flow imaging, the general movement or velocity of fluid (e.g., blood) or tissue is imaged in a flow image determined from a Doppler shift between transmitted and return ultrasound pulses. The flow image is conventionally displayed as an overlay or mapped on a B-mode image to view both an anatomical image and a flow velocity. Conventionally, the overlaid image is formed by replacing B-mode pixels with flow image pixels that are only above a set signal power.

However, the color flow imaging of conventional ultrasound imaging systems are limited along a single imaging or azimuth plane of the ultrasound probe. Due to the restriction of the conventional ultrasound imaging systems, the clinician must assure the blood flow of the anatomical structure being imaged is aligned along the imaging plane. Any tilts and/or shifts (e.g., along the elevation plane) of the ultrasound probe during the color flow imaging may result in an inaccurate measurement of the blood flow.

BRIEF DESCRIPTION OF THE INVENTION

In an embodiment, a method (e.g., for spatial color flow imaging) is provided. The method includes acquiring ultrasound data along a first two-dimensional (2D) plane and at least a second 2D plane from a matrix array probe for a region of interest (ROI). The first 2D plane extends along an azimuth plane and the second 2D plane extends along an elevation plane. The method further includes calculating a first flow velocity based on the ultrasound data along the first 2D plane, calculating a second flow velocity based on the ultrasound data along the second 2D plane, and generating a first color flow image based on the first flow velocity. The first color flow image includes a first set of graphical indicators representing the first flow velocity. The method further includes generating a second color flow image based on the second flow velocity. The second color flow image includes a second set of graphical indicators representing the second flow velocity. The method additionally includes generating an anatomical image based on the ultrasound data on a display, and overlaying the first and second color flow images to the anatomical image.

In an embodiment, a system (e.g., an ultrasound imaging system) is provided. The system includes a matrix array probe configured to acquire ultrasound data of a patient, a memory configured to store programmed instructions, and one or more processors configured to execute the programmed instructions stored in the memory. The one or more processors when executing the programmed instructions perform a plurality of operations. The one or more processors are configured to acquire ultrasound data along a first two-dimensional (2D) plane and at least a second 2D plane from a matrix array probe for a region of interest (ROI). The first 2D plane extends along an azimuth plane and the second 2D plane extends along an elevation plane. The one or more processors are further configured to calculate a first flow velocity based on the ultrasound data along the first 2D plane, calculate a second flow velocity based on the ultrasound data along the second 2D plane, and generate a first color flow image based on the first flow velocity. The first color flow image includes a first set of graphical indicators representing the first flow velocity. The one or more processors are further configured to generate a second color flow image based on the second flow velocity. The second color flow image includes a second set of graphical indicators representing the second flow velocity. The one or more processors are further configured to generate an anatomical image based on the ultrasound data on the display, and overlay the first and second color flow images to the anatomical image.

In an embodiment, a tangible and non-transitory computer readable medium comprising one or more computer software modules are provided. The one or more computer software modules are configured to direct one or more processors to acquire ultrasound data along a first two-dimensional (2D) plane and at least a second 2D plane from a matrix array probe for a region of interest (ROI). The first 2D plane extends along an azimuth plane and the second 2D plane extends along an elevation plane. The one or more computer software modules are further configured to direct one or more processors to calculate a first flow velocity based on the ultrasound data along the first 2D plane, calculate a second flow velocity based on the ultrasound data along the second 2D plane, and generate a first color flow image based on the first flow velocity. The first color flow image includes a first set of graphical indicators representing the first flow velocity. The one or more computer software modules are further configured to direct one or more processors to generate a second color flow image based on the second flow velocity. The second color flow image includes a second set of graphical indicators representing the second flow velocity. The one or more computer software modules are further configured to direct one or more processors to generate an anatomical image based on the ultrasound data on a display, and overlay the first and second color flow images to the anatomical image.

BRIEF DESCRIPTION OF THE DRAWINGS

FIG. 5 illustrates an embodiment of a color flow image.

DETAILED DESCRIPTION OF THE INVENTION

Figure 1:
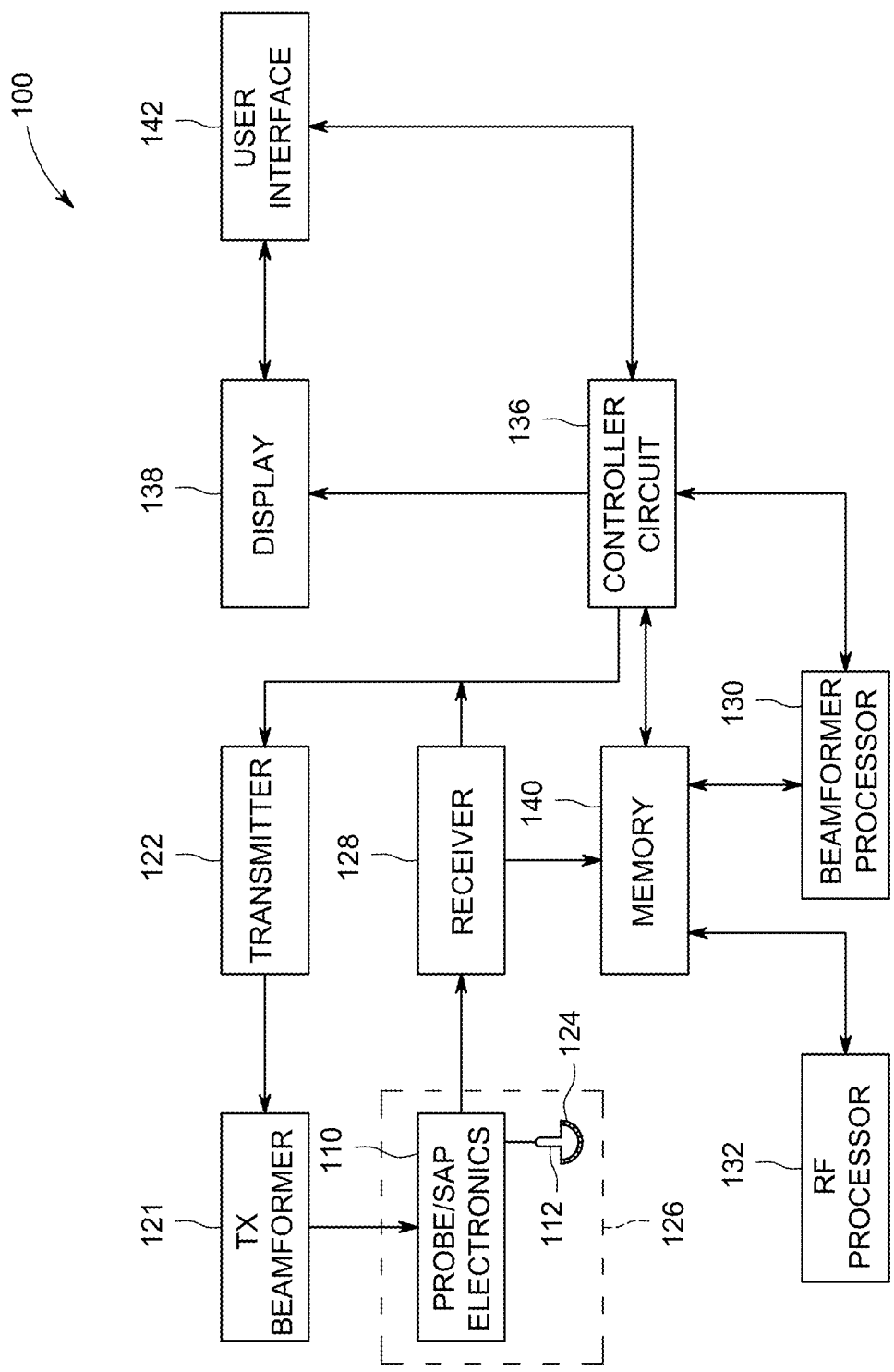
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for spatial color flow imaging for diagnostic medical imaging based on ultrasound data acquired along an azimuth and elevation planes. In operation, the diagnostic medical imaging may be an ultrasound imaging system having a matrix array probe having a two dimensional array of transducer elements. The matrix array probe may be configured to acquire ultrasound data such as blood flow data along two orthogonal two-dimensional (2D) planes, such as an azimuth and elevation planes relative to the ultrasound probe. The ultrasound imaging system may be configured to overlay the blood flow data from one or both of the azimuth and elevation planes on an anatomical image such as a B-mode image, M-mode, C-mode image, and/or the like. The blood flow data may be shown as one or more graphical indicators such as different colors, graphical icons, and/or the like. For example, the ultrasound imaging system may be configured to display the blood flow data corresponding to the elevation plane as graphical icons such as randomly seeded small bubbles, which illustrate the movement of blood flow along the elevation direction moving in real (or downscaled) velocity. A size of the graphical icon may change corresponding to position relative to the elevation plane.

Additionally or alternatively, the ultrasound imaging system may be configured to indicate to the clinician to reposition the ultrasound probe. For example, the ultrasound imaging system may display an indicator icon to indicate to the clinician a direction to adjust the mixed array probe to align the blood flow of the anatomical structure along one of the 2D planes.

In operation, the provided systems and methods select which pixels or voxels from a color flow image and an anatomical image to form an ultrasound image. The selection of the pixels or voxels is based on a calculated color flow power or Doppler power and a flow velocity corresponding to and/or represented by the pixels or voxels of the color flow image.

A technical effect of at least one embodiment described herein enables a clinician to correct for out of plane blood flow. A technical effect of at least one embodiment described herein enables a better origination for the clinician relative to conventional ultrasound imaging systems.

FIG. 1 is a schematic diagram of a diagnostic medical imaging system, specifically, an ultrasound imaging system 100. The ultrasound imaging system 100 includes an ultrasound probe 126 having a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from a region of interest (ROI) (e.g., organ, blood vessel, heart, brain, fetal tissue, cardiovascular, neonatal brain, embryo, abdomen, and/or the like) that includes one or more anatomical structures of the patient. For example, the ultrasound data may include anatomical information for imaging, measurements in changes in position or velocity within the ROI (e.g., flow velocity, movement of blood cells), difference in compression displacement of the tissue (e.g., strain), and/or for therapy, and/or the like. The ultrasound probe 126 is communicatively coupled to the controller circuit 136 via the transmitter 122. The transmitter 122 transmits a signal to a transmit beamformer 121 based on acquisition settings received by the controller circuit 136. The acquisition settings may define an amplitude, pulse width, frequency, and/or the like of the ultrasonic pulses emitted by the transducer elements 124. The transducer elements 124 emit pulsed ultrasonic signals into a patient (e.g., a body). The acquisition settings may be adjusted by the user by selecting a gain setting, power, time gain compensation (TGC), resolution, and/or the like from the user interface 142. The signal transmitted by the transmitter 122 in turn drives a plurality of transducer elements 124 within a transducer array 112. In connection with FIG. 2, the transducer array 112 may be a matrix array of transducer elements 124 arranged to include an elevation direction and an azimuth direction. For example only, the transducer array 112 may include an array of transducer elements 124 along the azimuth plane 206 and along the elevation plane 208 to from a matrix array probe (e.g., the ultrasound probe 126).

In various embodiments, the array of transducer elements 124 may not be equal along the azimuth and elevation planes 206, 208. For example, the transducer array 112 of the ultrasound probe 126 may be arranged as a 1.5-D array, a 1.75-D array, and/or the like. Additionally or alternatively, the array of transducer elements 124 may be equal along the azimuth and elevation planes 206, 208.

Figure 2:
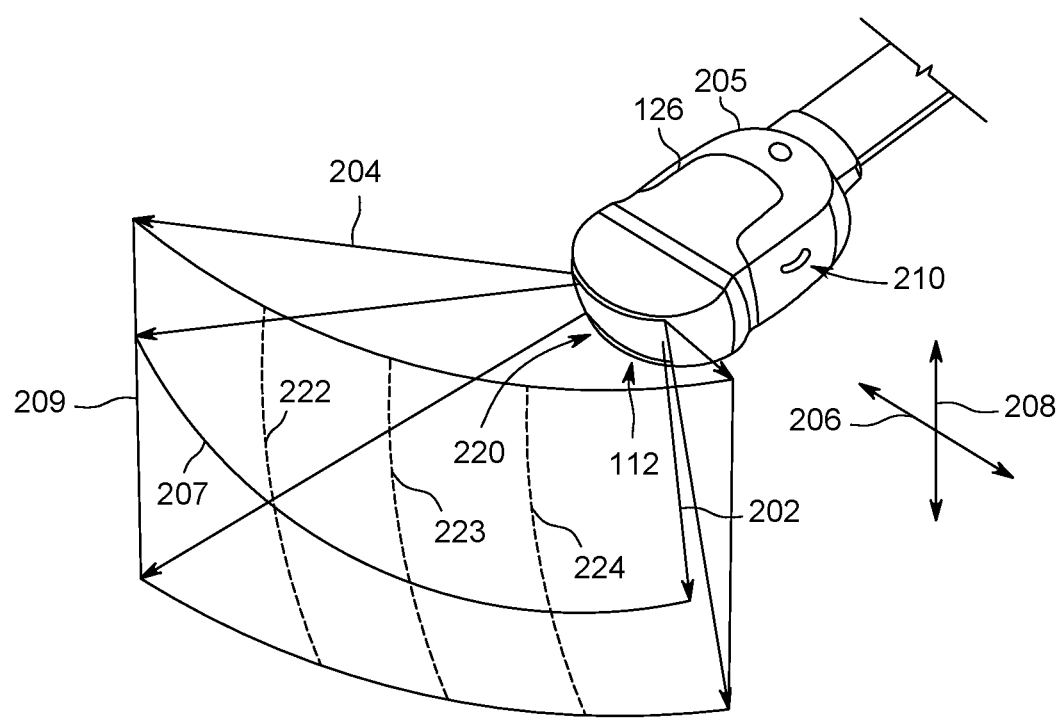
FIG. 2 is an illustration of two dimensional planes of an ultrasound probe of an embodiment of the ultrasound imaging system shown in FIG. 1.

FIG. 2 is an illustration of the 2D planes 202, 204 of the ultrasound probe 126 of an embodiment of the ultrasound imaging system 100. The 2D planes 202, 204 may each define a 2D area extending from the transducer array 112 of the ultrasound imaging system 100 for acquiring ultrasound data. The 2D planes 202, 204 are orthogonal with respect to each other. For example, the 2D plane 202 extends along the azimuth direction (e.g., parallel to an azimuth plane 206), and the 2D plane 204 extends along the elevation direction (e.g., parallel to an elevation plane 208). It may be noted that the 2D plane 202 may be positioned at different positons along the transducer array 112. For example, the 2D plane 202 may be positioned at different locations along the azimuth plane 206 of the transducer array 112. The 2D plane 202 extends along the azimuth plane 206 shown as a standard plane extending along a length of the transducer array 112 of the ultrasound probe 126. The 2D plane 204 extends along the elevation plane 208 shown as a vertical plane extending along a height of the transducer array 112 of the ultrasound probe 126.

The ultrasound probe 126 includes a housing 205 configured to enclose the probe/SAP electronics 110 and affix the transducer array 112 to a front end 220 of the ultrasound probe 126. The housing 205 may include one or more user interface components 210, such as a tactile button, rotary button, capacitive button, and/or the like. The front end 220 of the housing 205 shown in FIG. 2 is configured to hold and/or confine the transducer array 112, which is shown extending along the azimuth plane 206 of the housing 205. It may be noted a variety of a geometries and/or configurations may be used for the transducer array 112. For example, the transducer elements 124 of the transducer array 112 forms a curved surface area of the ultrasound probe 126 such that opposing ends of the transducer array 112 deviates from a center portion of the transducer array 112.

Returning to FIG. 1, the transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from the ROI (e.g., heart, left ventricular outflow tract, breast tissues, liver tissues, cardiac tissues, prostate tissues, neonatal brain, embryo, abdomen, and/or the like) to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the ROI (e.g., flow velocity, movement of blood cells), differences in compression displacement of the tissue (e.g., strain), and/or for therapy, among other uses. For example, the ultrasound probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored on memory 140, temporarily. The digitized signals correspond to the backscattered waves received by each transducer element 124 at various times. After digitization, the signals still may preserve the amplitude, frequency, phase information of the backscatter waves.

Optionally, the controller circuit 136 may retrieve the digitized signals stored in the memory 140 to prepare for the beamformer processor 130. For example, the controller circuit 136 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 140) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller circuit 136. For example, the operations described being performed by the beamformer processor 130 may be configured to be performed by the controller circuit 136.

In connection with FIG. 2, the beamformer processor 130 may be configured to acquire ultrasound data concurrently along the 2D planes 202, 204. During acquisition of the ultrasound data, the beamformer processor 130 is configured to beamform ultrasound data along the 2D planes 202, 204. For example, the beamformer processors 130 may be configured to define a first 2D plane and at least a second 2D plane to acquire ultrasound data along the 2D planes 202, 204. Based on the 2D planes 202, 204 the beamformer processor 130 may be configured to perform filtering and/or decimation, to isolate and/or select the digitized signals corresponding to select transducer elements 124 of the transducer array 112 defining the 2D planes 202, 204. The select transducer elements 124 represent active footprints selected for beamforming that define the 2D planes 202 and 204. The beamformer processor 130 may define channels and/or time slots of the digitized data that correspond to the selected transducer elements 124 that may be beamformed, with the remaining channels or time slots of digitized data (e.g., representing transducer elements 124 not within the active footprints representing the 2D planes 202, 204) that may not be communicated for processing (e.g., discarded). For example, the beamforming processor 130 may be configured to acquire ultrasound data along the 2D plane 202, and at least a second 2D plane such as the 2D planes 222, 223, and/or 224 parallel to the 2D plane 204. It may be noted that the ultrasound data acquired along the 2D planes 202 and 204 may be acquired concurrently and/or simultaneously by the ultrasound probe 126. It may be noted that the beamforming processor 130 may acquire ultrasound data along different positions of the 2D plane 202. For example, the beamformer processor 130 may be configured to acquire ultrasound data along 2D plane 204 at different positions relative to the 2D planes 222, 223, 224. Additionally or alternatively, the beamformer processor 130 is configured to process the digitized data corresponding to the transducer elements 124 defining the 2D plane 202 and the at least the second 2D planes 222, 223, and/or 224 along the 2D plane 204 concurrently and/or simultaneously.

Each of the 2D planes 202 and 204 extend along the azimuth plane 206 and the elevation plane 208 defining imaging angles 207, 209. For example, the imaging angle 207 of the 2D plane 202 extends along the azimuth direction, and the imaging angle 209 of the 2D plane 204 extends along the elevation direction. The imaging angles 207, 209 may correspond to a 2D sweep angle centered at a virtual apex defining a range along the azimuth and elevation planes 206, 208 from the transducer array 112 the controller circuit 136 is configured to acquire ultrasound data. A size (e.g., length along the azimuth direction, length along the elevation direction) of the imaging angles 207, 209 may be adjusted by the beamformer processor 130 and/or the controller circuit 136. For example, the size of the imaging angle 209 of the 2D plane 204 may correspond to an array of select transducer elements 124 along the elevation plane 208 to define the length of the imaging angle 209 selected by the beamformer processor 130. In another example, the controller circuit 136 may instruct the beamformer processor 130 to adjust the length based on instructions received from the user interface component 210 and/or a user interface 142. The controller circuit 136 may be configured to adjust a size of the imaging angle 207 by adjusting a number of transducer elements 124 along the azimuth plane 206 included in the digitized signals by the beamformer processor 130. In another example, the controller circuit 136 may be configured to adjust a size of the imaging angle 207 by adjusting a number of transducer elements 124 along the elevation plane 208 included in the digitized signals by the beamformer processor 130.

The beamformer processor 130 performs beamforming on the digitized signals and outputs a radio frequency (RF) signal. The RF signal is then provided to an RF processor 132 that processes the RF signal. The RF processor 132 may generate different ultrasound image data types, such as B-mode, color Doppler (e.g., velocity, power, variance), tissue Doppler (e.g., velocity), Doppler energy, and/or the like for multiple scan planes or different scanning patterns. For example, the RF processor 132 may generate tissue Doppler data for multi-scan planes (e.g., the 2D planes 222, 223, 224). The RF processor 132 gathers the information (e.g. I/Q, B-mode, color Doppler, tissue Doppler, and Doppler energy information) related to multiple data slices and stores the data information, which may include time stamp and orientation/rotation information, in the memory 140.

Alternatively, the RF processor 132 may include a complex demodulator (not shown) that demodulates the RF signal to form IQ data pairs representative of the echo signals. The RF or IQ signal data may then be provided directly to the memory 140 for storage (e.g., temporary storage). Optionally, the output of the beamformer processor 130 may be passed directly to the controller circuit 136.

The controller circuit 136 may be configured to process the acquired ultrasound data (e.g., RF signal data or IQ data pairs) and prepare frames of ultrasound image data for display on the display 138. The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140).

The controller circuit 136 is configured to perform one or more processing operations according to a plurality of selectable ultrasound modalities on the acquired ultrasound data, adjust or define the ultrasonic pulses emitted from the transducer elements 124, adjust one or more image display settings of components (e.g., ultrasound images, interface components, positioning regions of interest) displayed on the display 138, and other operations as described herein. Acquired ultrasound data may be processed in real-time by the controller circuit 136 during a scanning or therapy session as the echo signals are received. Additionally or alternatively, the ultrasound data may be stored temporarily in the memory 140 during a scanning session and processed in less than real-time in a live or off-line operation. Optionally, the controller circuit 136 may be a collection of circuits and/or software modules, but may be implemented utilizing any combination of dedicated hardware boards, DSPs, one or more processors, FPGAs, ASICs, a tangible and non-transitory computer readable medium configured to direct one or more processors, and/or the like.

For example, the controller circuit 136 may include circuits configured to process the IQ data pairs in a corresponding manner to generate, respectively, color flow data, ARFI data, B-mode data, spectral Doppler data, acoustic streaming data, tissue Doppler data, tracking data, electrography data (e.g., strain data, shear-wave data), among others, all of which may be stored in a memory 140 temporarily before subsequent processing. The data may be stored, for example, as sets of vector data values, where each set defines an individual ultrasound image frame. The vector data values are generally organised based on the polar coordinate system. The configured circuits may perform mid-processor operations representing one or more software features of the ultrasound imaging system 100. The controller circuit 136 may receive ultrasound data in one of several forms. In the embodiment of FIG. 1, the received ultrasound data may constitute IQ data pairs representing the real and imaginary components associated with each data sample of the digitized signals. The IQ data pairs are provided to one or more of the circuits of the controller circuit 136, for example, a color-flow circuit, an acoustic radiation force imaging (ARFI) circuit, a B-mode circuit, a spectral Doppler circuit, an acoustic streaming circuit, a tissue Doppler circuit, a tracking circuit, an electrography circuit, and/or the like. Other configured circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

The memory 140 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions (e.g., for the controller circuit 136, the beamformer processor 130, the RF processor 132), and/or the like. The memory 140 may be a tangible and non-transitory computer readable medium such as flash memory, RAM, ROM, EEPROM, and/or the like. The memory 140 may store ultrasound image data sets of the ultrasound data. For example, a 3D ultrasound image data set may be mapped into the corresponding memory 140, as well as one or more reference planes. The processing of the ultrasound data, including the ultrasound image data sets, may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored in the memory 140 or currently being acquired, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller circuit 136 shown on the display. The GUI may include one or more interface components that may be selected, manipulated, and/or activated by the user operating the user interface 142 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 100 performed by the controller circuit 136.

Figure 3A:
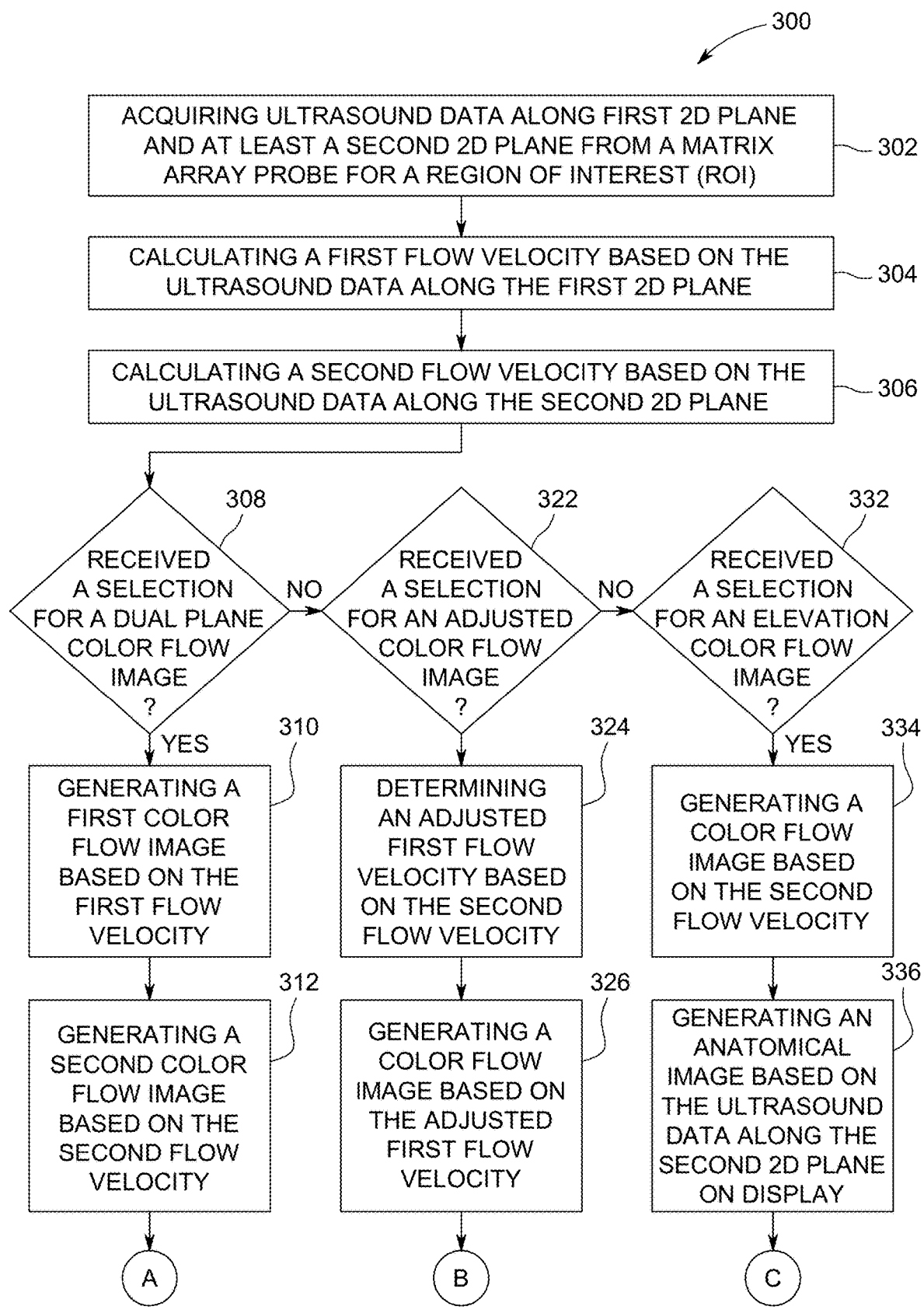
FIGS. 3A-B illustrate a flowchart of an embodiment of a method for spatial color flow imaging, in accordance with an embodiment.
Figure 3B:
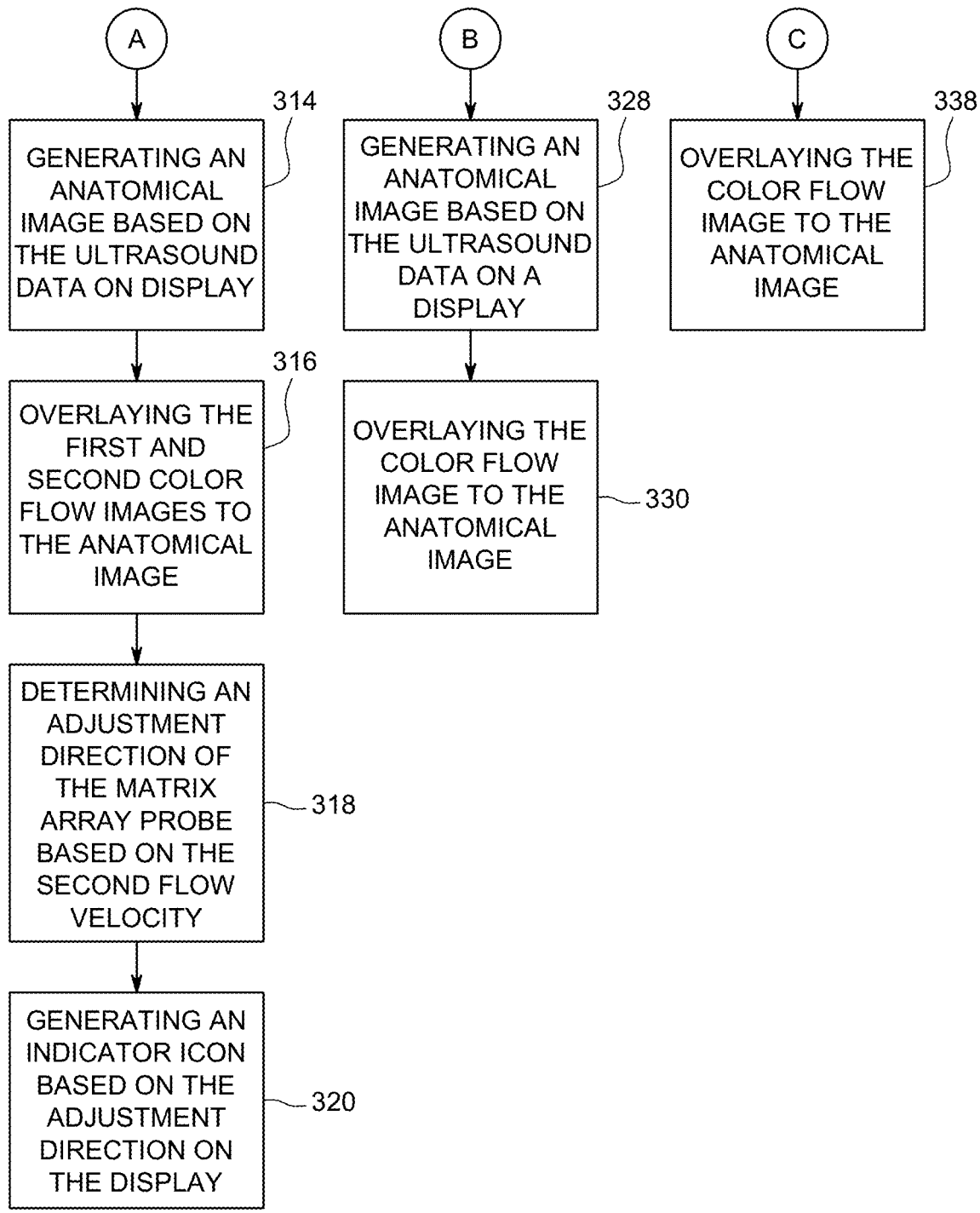

In connection with FIGS. 3A-B, the user may select an interface component corresponding to generate color mapped ultrasound image, which includes a color flow image based on ultrasound data having flor velocity information overlaid on an anatomical image using the user interface 142. When the interface component is selected, the controller circuit 136 may perform one or more of the operations described in connection with method 300.

FIGS. 3A-B illustrate a flowchart of an embodiment of a method 300 for spatial color flow imaging, in accordance with various embodiments described herein. The method 300, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms to direct hardware to perform one or more operations described herein. It should be noted, other methods may be used, in accordance with embodiments herein.

Beginning at 302, the controller circuit 136 may collect ultrasound data along the first 2D plane 202 and at least a second 2D plane from a matrix array probe (e.g., the ultrasound probe 126) for a region of interest (ROI). The first 2D plane 202 extends along the azimuth plane 206, and the at least second 2D plane (e.g., the 2D planes 222, 223, 224) extends along the elevation plane 208 defined by the 2D plane 204. The ROI may correspond to a cardiac structure, such as a heart, left ventricle, right ventricle, left ventricular outflow tract, vascular structure, and/or the like. The user may position the ultrasound probe 126 (FIG. 1) to align the transducer array 112, for example, at an abdominal view, a four-chamber, five-chamber, short-axis and three-vessel view, and/or the like of the heart. Ultrasound acquisition settings may configure the ultrasound probe 126 to collect ultrasound data of the ROI. The ultrasound acquisition settings may be defined based on signals received by the user interface 142. For example, the user may select one or more interface components displayed on the GUI and/or select keystrokes corresponding to instructions for the controller circuit 136, such as an interface component corresponding to color flow mapping, using the user interface 142 (FIG. 1).

The ultrasound data may include anatomical information for imaging, measurements in changes in position or velocity within the ROI (e.g., flow velocity, movement of blood cells), difference in compression displacement of the tissue (e.g., strain), and/or for therapy, and/or the like. For example, the controller circuit 136 may adjust the ultrasound acquisition settings (e.g., the gain, power, time gain compensation (TGC), resolution, and/or the like of the ultrasound probe 126) and process received ultrasound data. Based on the ultrasound acquisition settings, the transducer elements 124 may emit ultrasonic pulses over a period of time, of which, at least a portion may be to measure a position and/or velocity within the ROI (e.g., color flow imaging) and another portion for anatomical imaging (e.g., B-mode imaging, C-mode imaging, M-mode imaging, and/or the like).

In various embodiments, the ultrasonic pulses corresponding to the measuring of the position and/or flow velocity within the ROI (e.g., movement of blood cells) and the anatomical imaging may be interleaved. For example, the transducer elements 124 may transmit pulse sequences corresponding to the color flow imaging or the anatomical imaging. The pulse sequences may include tone bursts of a length P, and are fired repeatedly at a pulse repetition frequency (PRF) focused at a focal position along the first and second 2D planes 202, 204. In operation, the pulse sequences corresponding to the color flow imaging may be interposed between the pulse sequences corresponding to the anatomical imaging. For example, a color flow imaging pulse sequence may be transmitted subsequent to and preceding an anatomical imaging pulse sequence. It may be noted that the color flow image may be based on data acquired utilizing alternative modes of the ultrasound imaging system 100. For example, the color flow image may be based on the magnitude of data acquired utilizing the spectral Doppler mode of the controller circuit 136.

At least a portion of the ultrasonic pulses are backscattered by the tissue of the ROI and received by the receiver 128, which converts the received echo signals into digitized signals. The digitized signals, as described herein, are beamformed by the beamformer processor 130 and formed into IQ data pairs (e.g., the ultrasound data) representative of the echo signals by the RF processor 132. The controller circuit 136 may instruct the beamformer processor 130 to select digitized signals received from the ultrasound probe 126 corresponding to the first 2D plane 202, and at least a second 2D plane (e.g., the 2D planes 222, 223, 224) along the 2D plane 204 (Shown in FIG. 2). The select digitized signals may correspond to transducer elements aligned along the azimuth plane 206 and elevation plane 208 corresponding to the 2D plane 202 and 204, respectively. For example, the beamformer processor 130 may be configured to perform filtering and/or decimation, to isolate and/or select the digitized signals corresponding to the relevant transducer elements 124 of the transducer array 112 along the 2D planes 202, 204 representing active footprints selected for beamforming. The digitized signals are beamformed by the beamformer processor 130, and output the RF signal processed to the RF processor 132. The processed RF signals are stored as ultrasound data in the memory 140, which is acquired and received by the controller circuit 136. The ultrasound data may be stored in the memory as pixels for one or more frames for color flow imaging, anatomical imaging, and/or the like.

At 304, the controller circuit 136 may be configured to calculate a first flow velocity based on the ultrasound data along the first 2D plane 202. For example, the controller circuit 136 may calculate a first flow velocity for each pixel represented as the ultrasound data acquired along the first 2D plane 202. The pixels may be an array of pixels forming one or more frames corresponding to the color flow image data generated by the controller circuit 136. Each of the pixels may represent and/or include information corresponding to the first flow velocity along the first 2D plane 202.

For example, the controller circuit 136 may receive the ultrasound data stored in the memory 140 collected in response to the pulse sequences of the color flow imaging emitted by the ultrasound probe 126 along the first 2D plane 202. The controller circuit 136 may perform filtering (e.g., wall filter, high pass filter, band-pass filter) to remove or reject stationary or slow-moving tissue from the ultrasound data to decrease a processing load on the controller circuit 136. The controller circuit 136 may convert the received ultrasound data into intermediate parameters N, D, and R(0) for locations or range cells of the ROI, which may correspond to resulting pixels. R(0) may be an estimate of the returned power or Doppler signal power of the received echo signals calculated by the filtered ultrasound data, for example, the ultrasound data may be IQ data pairs calculated by the RF processors 132 stored in the memory 140, as shown in Equation 1. R(0) is approximated as a finite sum over a number of pulse sequences (e.g., represented by the variable M) at a position within the ROI along the first 2D plane 202.

$$R(0) = \sum_{i=1}^{M-1} \frac{(I_i^2 + Q_i^2 + I_{i+1}^2 + Q_{i+1}^2)}{2} \quad \text{(Equation 1)}$$

The controller circuit 136 is configured to calculate the first flow velocity (e.g., movement of the tissue with respect to the ultrasound probe 126, blood flow) along the first 2D plane 202 of the ultrasound probe 126 for multiple vector positions and multiple range gates within the tissue based on phase shifts of the digitized signals with respect to the transmitted ultrasound pulses. The flow velocity may be based on the variables N and D calculated by the controller circuit 136 as shown below in Equations 2 and 3 to determine a phase shift as shown in Equation 4. The variable T corresponding to the pulse repetition time between each pulse in the pulse sequence corresponding to the color flow imaging along the first 2D plane 202.

$$N = \sum_{i=1}^{M-1} (I_i Q_{i+1} - I_{i+1} Q_i) \quad \text{(Equation 2)}$$

$$D = \sum_{i=1}^{M-1} (I_i I_{i+1} + Q_i Q_{i+1}) \quad \text{(Equation 3)}$$

$$\phi(R(T)) = \tan^{-1}\left[\frac{N}{D}\right] \quad \text{(Equation 4)}$$

The controller circuit 136 may use the phase to calculate a mean Doppler frequency, as shown in Equation 5, which is proportional to the flow velocity as shown in the Doppler shift equation of Equation 6. The angle represented by θ is the Doppler angle. Optionally, in connection with FIG. 4, the vector data values may include pixel color information, such as red and blue, to represent a speed and a direction (e.g., with respect to the ultrasound probe 126) of the flow velocity.

$$\bar{f} = \frac{1}{2\pi T}(\phi(R(T))) \quad \text{(Equation 5)}$$

$$\bar{v} = \frac{\bar{f}}{f_0} \cdot \frac{c}{2\cos\theta} \quad \text{(Equation 6)}$$

At 306, the controller circuit 136 may be configured to calculate a second flow velocity based on the ultrasound data along the second 2D plane (e.g., the 2D planes 222, 223, and/or 224). For example, similar to and/or the same as 304, the controller circuit 136 may calculate the second flow velocity based on Equations 1-6. The controller circuit 136 may calculate a second flow velocity for each pixel represented as the ultrasound data acquired along the at least one second 2D plane, such as the 2D planes 222, 223, and/or 224 along the 2D plane 204.

It may be noted that operations at 304 and 306 may be based on ultrasound data acquired by the ultrasound probe 126 at a first position of the patient and/or during a single scan of the ROI by the ultrasound imaging system 100.

At 308, the controller circuit 136 may be configured to determine if a selection for a dual plane color flow image is received. The dual plane color flow image may represent an ultrasound image that includes velocity information of the ROI along the 2D planes 202, 204. The controller circuit 136 may be configured to determine if the dual plane color flow image is selected based on a user selection received from the user interface 142. For example, the controller circuit 136 may generate a GUI on the display 138. The GUI includes one or more interface components representing one or more options to view the color imaging based on the ultrasound data. One of the interface components may correspond to the dual plane color flow image. The user may select the interface component utilizing the user interface 142. Based on the selection of the interface component, the controller circuit 136 may determine that the dual plane color flow image was selected.

Figure 4A:
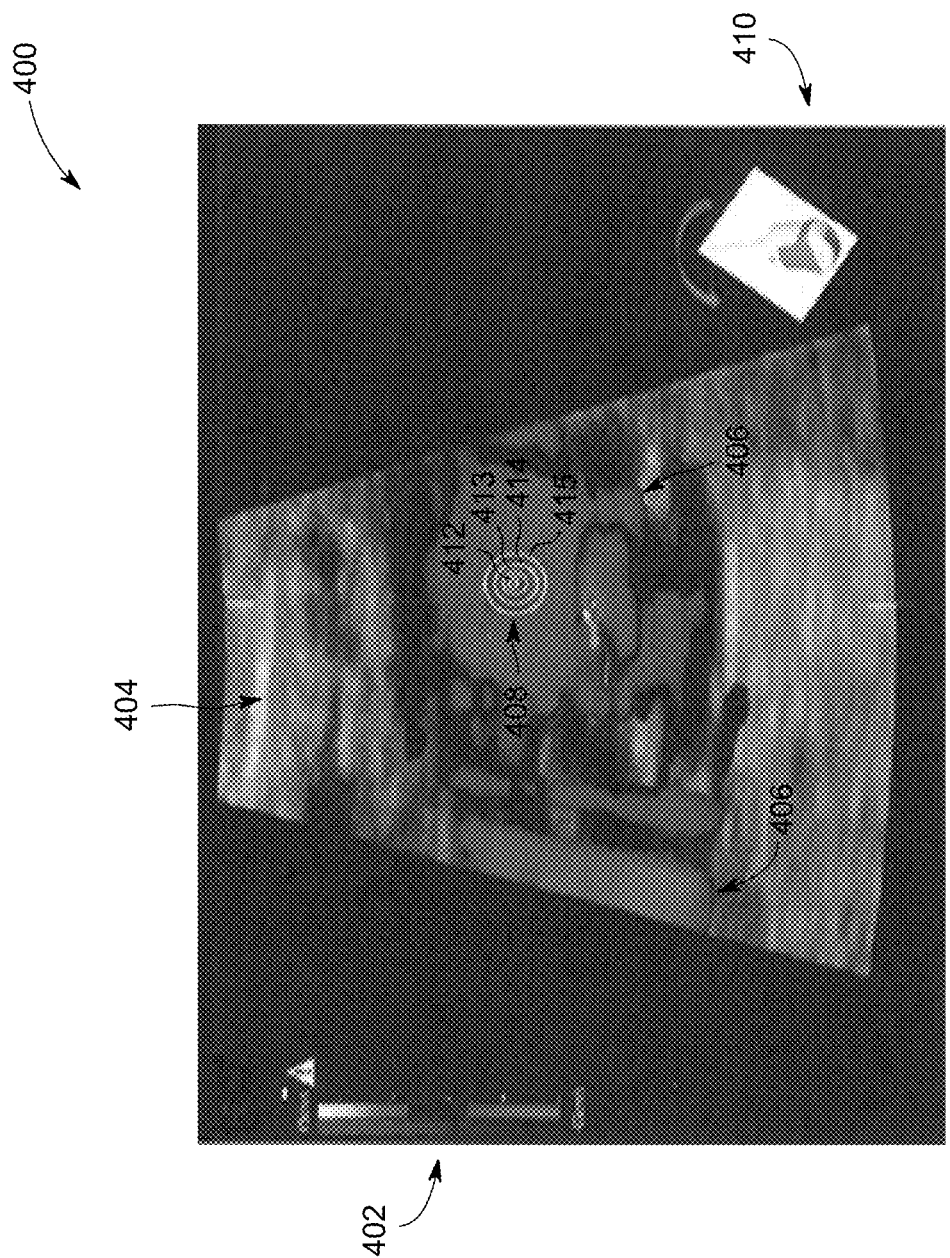
FIG. 4A-E illustrate embodiments of a dual plane color flow image.
Figure 4B:
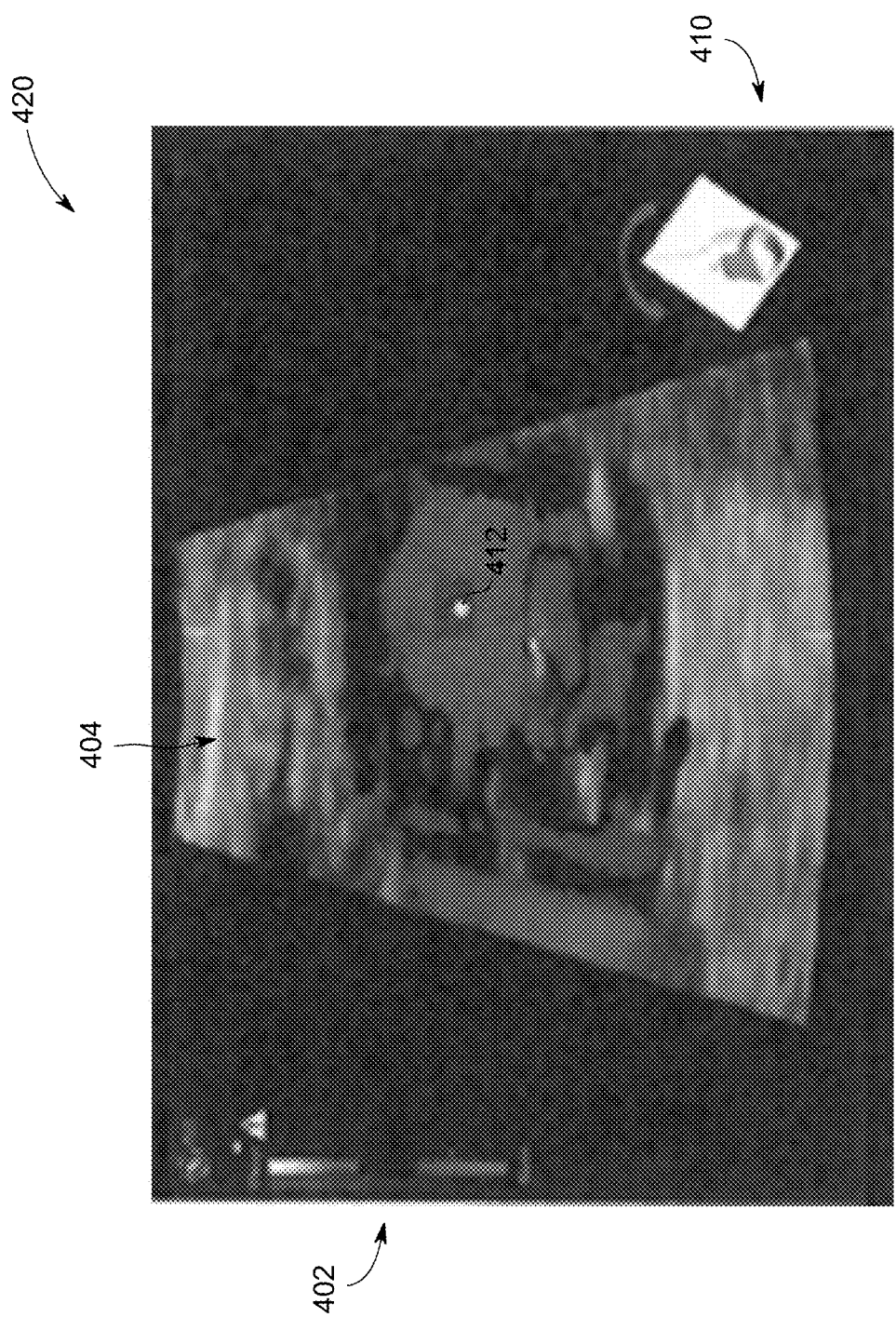
Figure 4C:
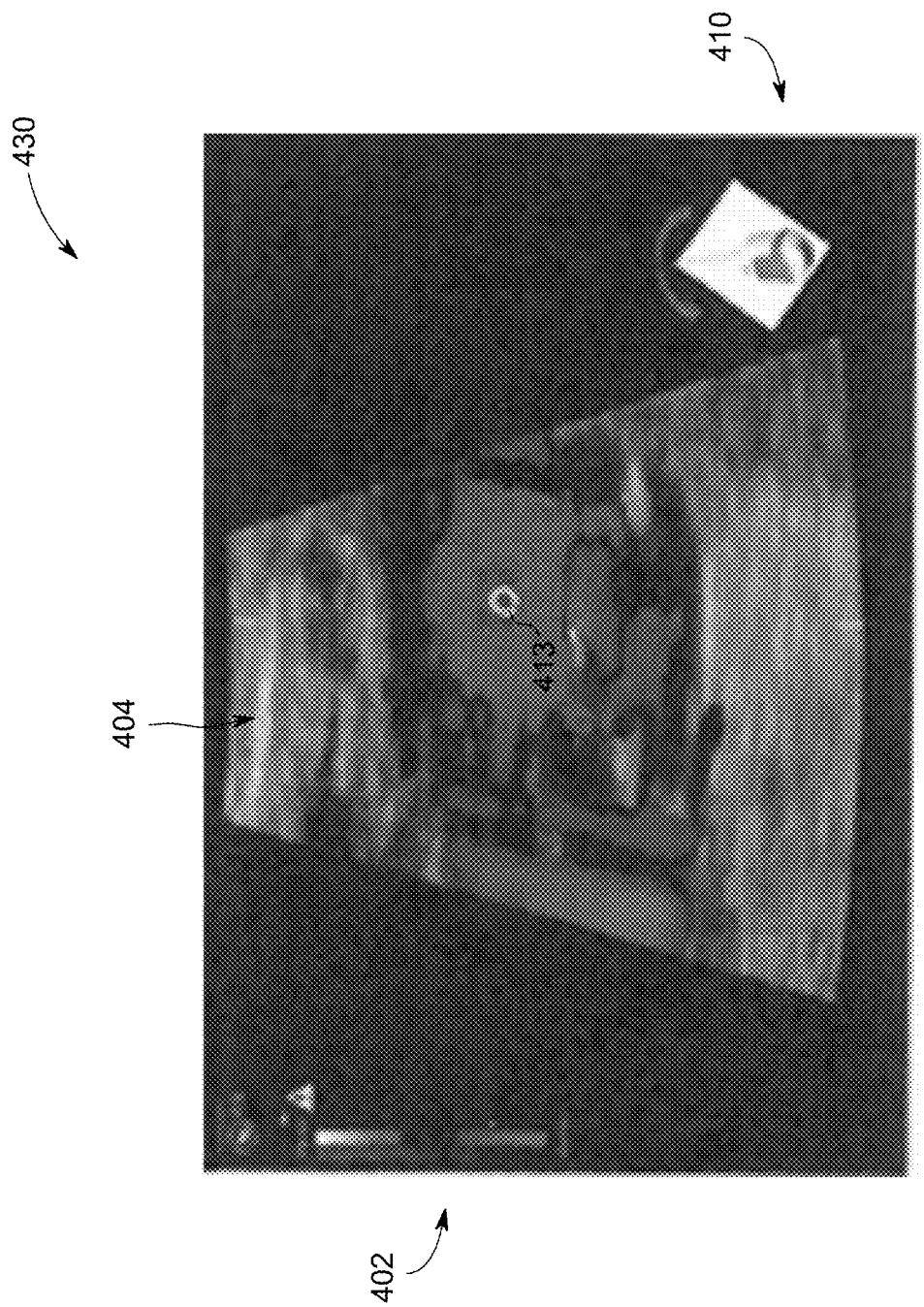
Figure 4D:
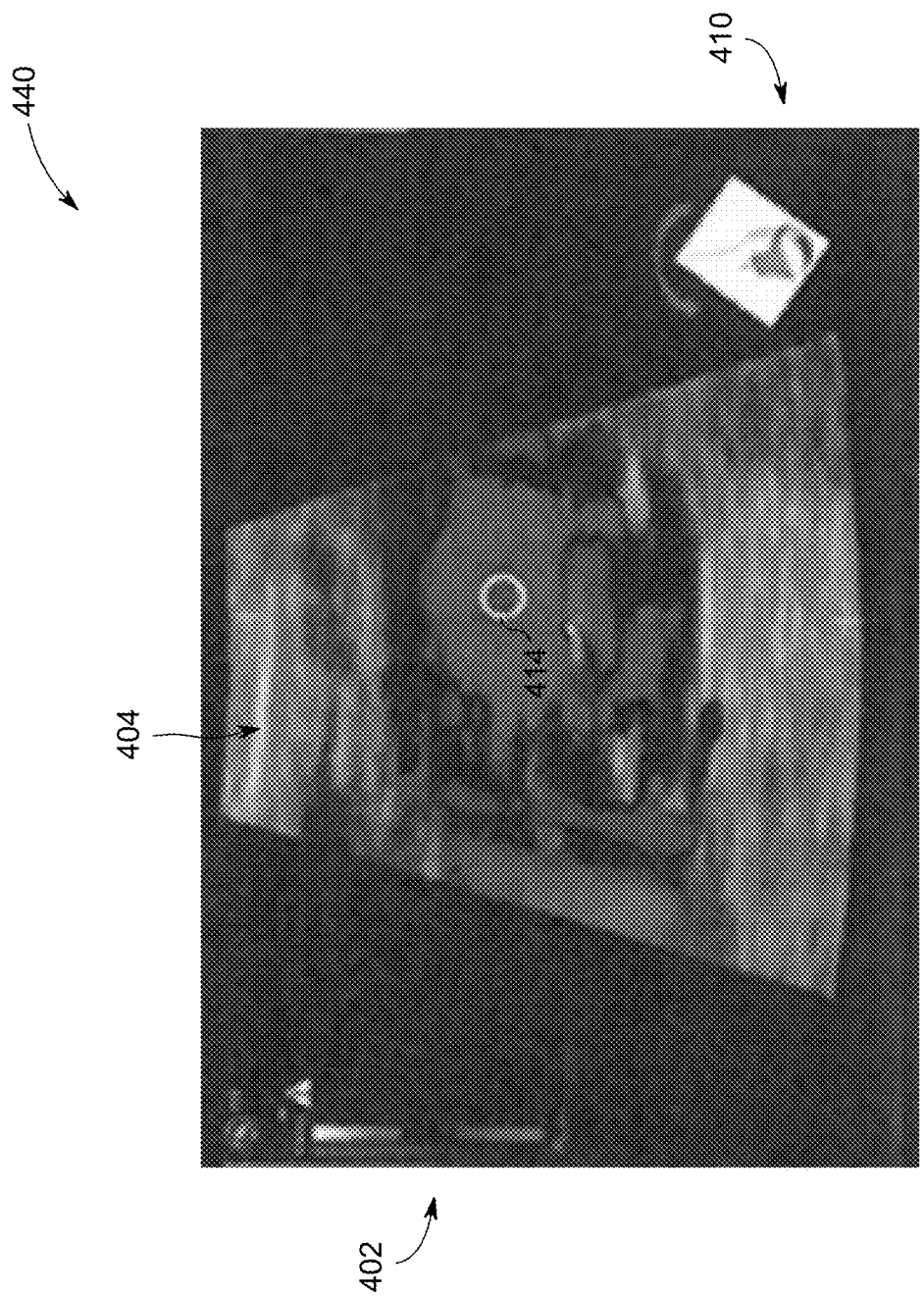
Figure 4E:
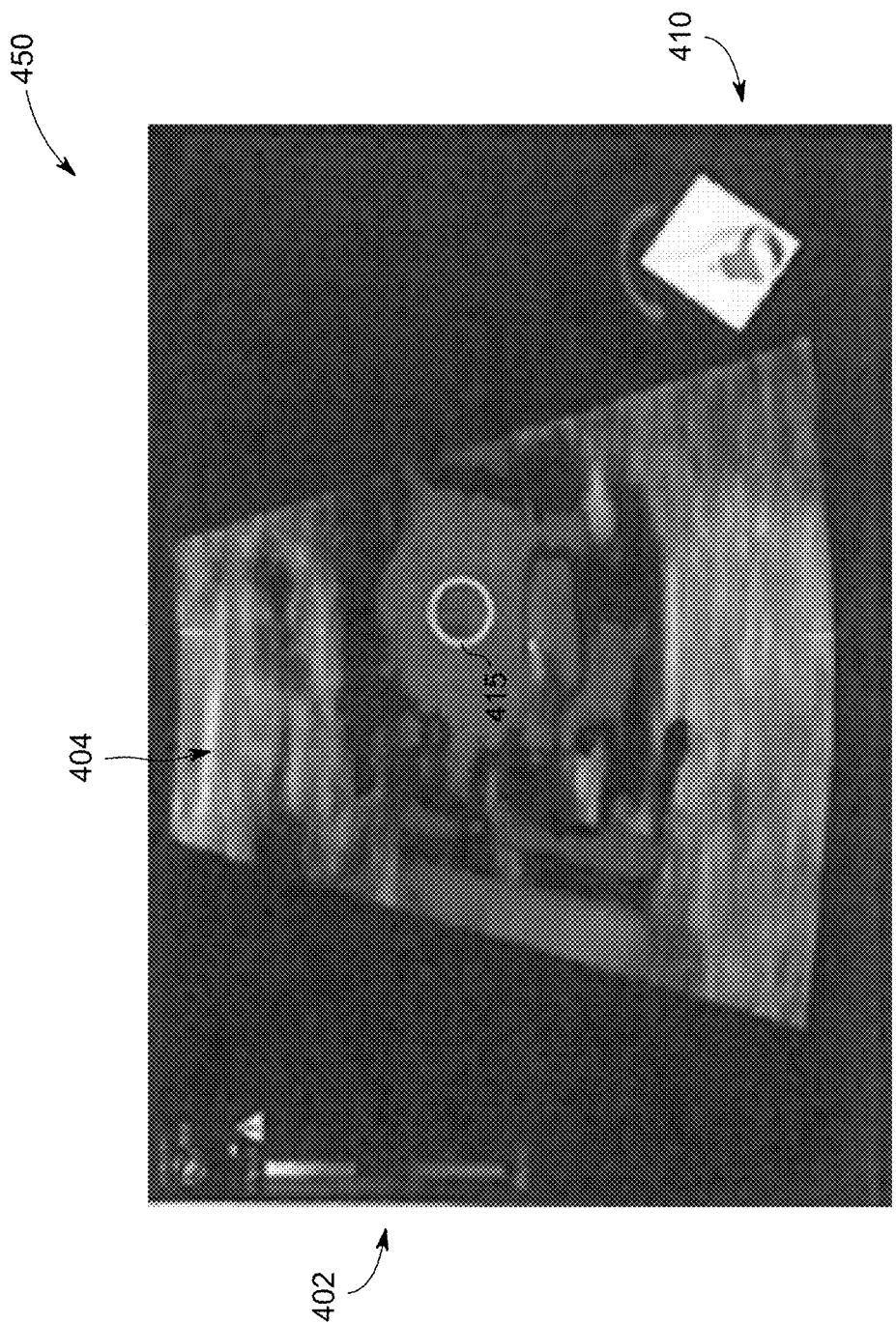

If the dual plane color image is selected, then at 310, the controller circuit 136 may be configured to generate a first color flow image 406 based on the first flow velocity. FIG. 4A illustrates an embodiment of a dual plane color flow image 400. The dual plane color flow image 400 includes a first color flow image 406, a second color flow image 408, and an anatomical image 404. The first color flow image 406 may be generated by the controller circuit 136 based on the vector data values stored in the memory 140. For example, the vector data value may include pixel values utilized by the controller circuit 136 to generate the first color flow image 406.

The pixel values of the first color flow image 406 includes a first set of graphical indicators representing the first flow velocity. The graphical indicators may be a color spectrum (as shown in FIG. 4A), graphical icons (e.g., circles, arrows, bubbles), textual information, and/or the like configured to represent the first flow velocity. For example, the first flow velocity of the first color flow image 406 is represented by a color of the pixel, such as red and blue, to represent a speed and a direction (e.g., with respect to the transducer array 112 along the first 2D plane 202) of the first flow velocity based on a color meter 402. The color meter 402 represents a graphical indicator of a defined color spectrum, which relates or associates a pixel color of the first color flow image 406 with a corresponding speed (e.g., cm/s) and direction of the first flow velocity along the first 2D plane 202.

At 312, the controller circuit 136 may be configured to generate the second color flow image 408 based on the second flow velocity. The second color flow image 408 may be generated by the controller circuit 136 based on the vector data values stored in the memory 140. For example, the vector data values may include pixel values utilized by the controller circuit 136 to generate the second color flow image 408. The pixel values are generated by the controller circuit 136 as the second color flow image 408. The pixel values of the second color flow image 408 may include a second set of graphical indicators 412-415 representing the second flow velocity. The second set of graphical indicators 412-415 are shown as corresponding graphical icons. A size and position of the graphical indicators 412-415 is based on the second flow velocity and position along the second 2D plane 204. For example, as the flow of the ROI (e.g., blood cells) crosses, traverses through, and/or approaches the 2D planes 222, 223, and/or 224, the controller circuit 136 increases a size of the graphical indicators 412-415.

In connection with FIGS. 4B-E, the graphical indicators 412-415 may be cycled by the controller circuit 136 representing an animation over time by sequentially and/or successively transition between the graphical indicators 412-415 to show the second flow velocity. For example, the animation of the successive transitions between the graphical indicators 412-415 may illustrate the second flow velocity traversing away, crossing, and/or towards the at least one 2D planes 222, 223, and/or 224.

FIGS. 4B-E illustrate dual plane color flow images 420, 430, 440, 450 illustrating the animation and/or transitions of the graphical indicators 412-415 over time. For example, the controller circuit 136 may continually transition successively and repeat the dual plane color flow images 420, 430, 440, 450. The transitions of the graphical indicators 412-415 by the controller circuit 136 increases a diameter and/or size of the graphical indicators 412-415. For example, the controller circuit 136 may continually increase a size of the graphical indicators 412-415 overtime. The change in size of the graphical indicators 412-415 are configured to indicate to the clinician (e.g., user) a direction of the second flow velocity relative to at least one of the 2D planes 222, 223, and/or 224. For example, the graphical indicators 412-415 shown in the dual plane color flow images 420, 430, 440, 450 successively shown having a larger size and/or diameter indicate the second flow velocity is directed towards at least one of the 2D planes 222, 223, and/or 224.

Additionally or alternatively, a rate of the transitions of the graphical indicators 412-415 may be based on a magnitude of the second flow velocity. For example, when the controller circuit 136 determines an increase in the second flow velocity, the controller circuit 136 is configured to increase the rate of the transition of the graphical indicators 412-415 of the dual plane color flow images 420, 430, 440, 450.

At 314 (shown in FIG. 3B), the controller circuit 136 may be configured to generate the anatomical image 404 based on the ultrasound data on the display 138. The anatomical image 404 may represent one or more modalities, such as a B-mode image, M-mode image, and/or the like. The anatomical image 404 may be generated by the controller circuit 136 based on the vector data values stored in the memory 140 acquired based on ultrasound signals representing anatomical information. For example, the vector data value may include pixel values utilized by the controller circuit 136 to generate the anatomical image 404.

At 316, the controller circuit 136 may be configured to overlay the first and second color flow images 406, 408 to the anatomical image 404. In connection with FIGS. 4A-E, the controller circuit 136 may overlay and/or superimpose the first and second color flow images 406, 408 to the anatomical image 404 such that each of the images 404, 406, 408 are shown concurrently and/or simultaneously to produce the dual plane color flow image 400. Additionally or alternatively, the controller circuit 136 may be configured to display the first and second color flow images 406, 408 and the anatomical image 404 concurrently in separate windows shown on the display 138.

At 318, the controller circuit 136 may be configured to determine an adjustment direction of the matrix array probe (e.g., ultrasound probe 126) based on the second flow velocity. The adjustment direction corresponds to a change in position (e.g., tilt angle) of the ultrasound probe 126 such that a direction of the second flow velocity is aligned along the first 2D plane 202. Additionally or alternatively, the adjustment direction may correspond to a change in position of the ultrasound probe 126 such that a direction of the first flow velocity is aligned along the second 2D plane 204.

The adjustment direction may be utilized by the clinician to correct for out of plane flow relative to one of the 2D planes 202, 204. For example, the controller circuit 136 may determine an adjustment angle representing a direction and/or position of the second flow velocity relative to the first 2D plane 202. Based on the adjustment angle, the controller circuit 136 is configured to calculate a direction the transducer array 112 and/or generally the ultrasound probe 126 would need to be adjusted (e.g., tilted) relative to the patient for the second flow velocity to be aligned with the first 2D plane 202. For example, the adjustment angle may correspond to a position (e.g., tilt angle) of the ultrasound probe 126 such that the second flow velocity is approximately zero and/or at a minimum magnitude relative to other positions of the ultrasound probe 126.

At 320, the controller circuit 136 may be configured to generate an indicator icon 410 based on the adjustment direction on the display 138. The indicator icon 410 may be a graphical icon (e.g., arrow), an animation, text, and/or the like shown on the display 138. The indicator icon 410 is configured by the controller circuit 136 to indicate a direction and/or position the ultrasound probe 126 would need to be adjusted for the first and second flow velocities to be aligned along one of the 2D planes 202, 204. In connection with FIG. 4, the indicator icon 410 may include a representation of the ultrasound probe and/or an arrow. The arrow is configured to indicate a direction of rotation of the ultrasound probe 126 based on the adjustment direction.

Additionally or alternatively, the controller circuit may generate an indicator icon (not shown) configured to indicate a change in second flow velocity. The indicator icon may be based on the change the second flow velocity due to a change in position of the ultrasound probe 126 over time. The indicator icon may be a numerical value, a graphical icon (e.g., arrow), textual information, and/or the like. For example, the clinician may adjust a position (e.g., tilt angle) of the ultrasound probe 126 relative to the patient during the scan. The controller circuit 136 may calculate a change in the second flow velocity based on the change in position of the ultrasound probe 126. Based on the indicator icon, the clinician may re-adjust and/or re-position the ultrasound probe 126 to minimize and/or reduce the second flow velocity.

If the dual plane color image is not received, then at 322 (shown in FIG. 3A), the controller circuit 136 may be configured to determine if a selection for an adjusted color flow image is received. The adjusted color flow image may represent an ultrasound image that includes adjusted velocity information (e.g., flow velocity) of the ROI along one of the 2D planes 202, 204. In connection with FIG. 5, the adjusted color flow image may include the first and second flow velocities acquired along the 2D planes 202, 204. The controller circuit 136 may be configured to determine if the adjusted color flow image is selected based on a user selection received from the user interface 142. For example, the controller circuit 136 may generate a GUI on the display 138. The GUI includes one or more interface components representing one or more options to view the color imaging based on the ultrasound data. One of the interface components may correspond to the adjusted color flow image. The user may select the interface component utilizing the user interface 142. Based on the selection of the interface component, the controller circuit 136 may determine that the adjusted color flow image was selected.

At 324, the controller circuit 136 may be configured to determine an adjusted first color flow velocity based on the second flow velocity. The adjusted first color flow velocity is configured to include and/or account for the second flow velocity acquired along the 2D plane 204 (e.g., the at least one 2D plane 222, 223, and/or 224). For example, the controller circuit 136 may determine select locations of the ROI. The select locations include both first and second color flow velocities based on vector data values. For example, the red blood cells of the ROI at the select locations traverses along the 2D planes 202, 204. The select locations may represent structures within the ROI that extend along the 2D planes 202, 204, such as a curved structure.

At the select locations, the controller circuit 136 may be configured to adjust the first color flow velocity to include the second flow velocity. For example, the controller circuit 136 may define vectors at the select locations based on the first and second flow velocities. The controller circuit 136 may determine the adjusted first color flow velocity by adding the vectors at one of the select locations. For example, the controller circuit 136 determines a first vector representing a first flow velocity of 3 cm/s, and a second vector representing a second flow velocity of 2 cm/s at a first select location based on the vector data values in the memory 140. The first and second vectors are orthogonal to each other based on the first and second 2D planes 202, 204. The controller circuit 136 may combine the first and second vectors to determine the adjusted first flow velocity at the first location. For example, the controller circuit 136 may determine a magnitude of the combined first and second vectors to be approximately 3.6 cm/s, which represents the adjusted first flow velocity. The controller circuit 136 may adjust the vector data values acquired along the first 2D plane 202 based on the adjusted first flow velocity. For example, the controller circuit 136 may adjust the pixel values representing a magnitude of the first flow velocity to the adjusted first flow velocity.

It may be noted in an embodiment, the controller circuit 136 may be configured to determine an adjusted second flow velocity based on the first flow velocity. For example, the adjusted second flow velocity may be calculated based on a selection by the clinician using the user interface 142. The second flow velocity may be calculated similar to and/or the same as the adjusted first flow velocity, for example, by calculated vectors representing the first flow velocity and the second flow velocity at one of the select locations.

At 326, the controller circuit 136 may be configured to generate a color flow image 506 based on the adjusted first color flow velocity. FIG. 5 illustrates an embodiment of the color flow image 506. The color flow image 406 may be generated by the controller circuit 136 based on the vector data values stored in the memory 140 representing the adjusted first flow velocity. For example, the vector data value may include pixel values utilized by the controller circuit 136 to generate the color flow image 406.

The pixel values of the color flow image 506 includes a first set of graphical indicators representing the adjusted first flow velocity. The graphical indicators may be a color spectrum (as shown in FIG. 5), graphical icons (e.g., circles, arrows, bubbles), textual information, and/or the like configured to represent the adjusted first flow velocity. For example, the adjusted first flow velocity of the color flow image 506 is represented by a color of the pixel, such as red and blue, to represent a speed and a direction of the adjusted first flow velocity based on a color meter 502. The color meter 502 represents a graphical indicator of a defined color spectrum, which relates or associates a pixel color of the color flow image 506 with a corresponding speed (e.g., cm/s) and direction of the adjusted first flow velocity. It may be noted that the direction of the adjusted first flow velocity is shown along the 2D plane 202, the adjusted first flow velocity includes the second flow velocity along the 2D plane 204 (e.g., the at least one 2D plane 222, 223, 224).

At 328 (shown in FIG. 3B), the controller circuit 136 may be configured to generate an anatomical image based on the ultrasound data on the display 138. The anatomical image 504 shown in FIG. 5 may represent one or more modalities, such as a B-mode image, M-mode image, and/or the like. The anatomical image 504 may be generated by the controller circuit 136 based on the vector data values stored in the memory 140 acquired based on ultrasound signals representing anatomical information. For example, the vector data value may include pixel values utilized by the controller circuit 136 to generate the anatomical image 504.

At 330, the controller circuit 136 may be configured to overlay the color flow image to the anatomical image. In connection with FIG. 5, the controller circuit 136 may overlay and/or superimpose the color flow image 506 to the anatomical image 504 such that each of the images 504, 506 are shown concurrently and/or simultaneously to produce an ultrasound image 500. Additionally or alternatively, the controller circuit 136 may be configured to display the color flow image 506 and the anatomical image 504 concurrently in separate windows shown on the display 138.

If the dual plane color image is not received, then at 332 (shown in FIG. 3A), the controller circuit 136 may be configured to determine if a selection for an elevation color flow image is received. The elevation color flow image may represent an ultrasound image that includes ultrasound data of the ROI along the second 2D plane 204, for example, the ultrasound data acquires by at least one 2D plane 222, 223, and/or 224. The controller circuit 136 may be configured to determine if the elevation color flow image is selected based on a user selection received from the user interface 142. For example, the controller circuit 136 may generate a GUI on the display 138. The GUI includes one or more interface components representing one or more options to view the color imaging based on the ultrasound data. One of the interface components may correspond to the elevation color flow image. The user may select the interface component utilizing the user interface 142. Based on the selection of the interface component, the controller circuit 136 may determine that the elevation color flow image was selected.

At 334, the controller circuit 136 may be configured to generate a color flow image based on the second color flow velocity. The color flow image may be generated by the controller circuit 136 based on the vector data values stored in the memory 140 acquired along the second 2D plane 204. For example, the vector data value may include pixel values utilized by the controller circuit 136 to generate the elevation color flow image. The pixel values representing the elevation color flow image are generated by the controller circuit 136 and may include and/or correspond to a set of graphical indicators representing the second flow velocity. Optionally, the set of graphical indicators may be similar to and/or the same as the graphical indicators of the first color flow image 406 shown in FIG. 4.

At 336, the controller circuit 136 may be configured to generate an anatomical image based on the ultrasound data along the second 2D plane on the display 138. For example, the anatomical image may represent a C-mode image acquired along the elevation plane, such as by at least one of the 2D planes 222, 223, 224. The anatomical image may be generated by the controller circuit 136 based on the vector data values stored in the memory 140 acquired based on ultrasound signals representing anatomical information. For example, the vector data value may include pixel values utilized by the controller circuit 136 to generate the anatomical image.

At 338 (shown in FIG. 3B), the controller circuit 136 may be configured to overlay the color flow image to the anatomical image. For example, the controller circuit 136 may overlay and/or superimpose the elevation color flow image to the anatomical image such that each of the images are shown concurrently and/or simultaneously to produce an ultrasound image. Additionally or alternatively, the controller circuit 136 may be configured to display the elevation color flow image and the anatomical image concurrently in separate windows shown on the display 138.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "circuit," "controller circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the "computer," "subsystem," "circuit," "controller circuit," or "module" as a processing machine to perform specific operations such as the methods and processes of the various embodiments. The set of instructions may be in the form of a software program and/or software module(s). The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for spatial color flow imaging, the method comprising:
    acquiring ultrasound data along a first two-dimensional (2D) plane and a second 2D plane from a matrix array probe for a region of interest (ROI), wherein the first 2D plane is orthogonal to the second 2D plane;
    calculating a first flow velocity within the ROI based on the ultrasound data along the first 2D plane;
    calculating a second flow velocity within the ROI based on the ultrasound data along the second 2D plane;
    generating a color flow image based on the first flow velocity;
    generating a set of graphical indicators based on the second flow velocity;
    generating and displaying an anatomical image on a display, the anatomical image based on the ultrasound data acquired along the first 2D plane; and
    overlaying the color flow image and the set of graphical indicators on the anatomical image on the display, wherein the set of graphical indicators are displayed as an animated repeating sequence that successively cycles between different graphical indicators in the set to represent the second flow velocity.

2. The method for spatial color flow imaging of claim 1, wherein the color flow image includes a color spectrum that represents the first flow velocity.

3. The method for spatial color flow imaging of claim 1, further comprising:
    determining an adjustment direction of the matrix array probe based on the second flow velocity, the adjustment direction corresponding to a change in tilt angle of the matrix array probe to enable alignment of the second flow velocity with one of the first 2D plane or the second 2D plane; and
    generating and displaying an indicator icon on the display, the indicator icon indicating the adjustment direction.

4. The method for spatial color flow imaging of claim 1, wherein the graphical indicators in the set have different sizes and are concentric.

5. The method for spatial color flow imaging of claim 1, wherein a rate at which the graphical indicators in the set are successively cycled represents a magnitude of the second flow velocity.

6. The method for spatial color flow imaging of claim 1, wherein an order at which the graphical indicators in the set are successively cycled represents a direction of the second flow velocity relative to the first 2D plane.

7. The method for spatial color flow imaging of claim 1, wherein the first flow velocity and the second flow velocity are measurements of blood flow through the ROI.

8. The method for spatial color flow imaging of claim 1, wherein the first 2D plane extends along an azimuth plane and the second 2D plane extends along an elevation plane.

9. An ultrasound imaging system comprising:
    a matrix array probe configured to acquire ultrasound data of a patient;
    a memory configured to store programmed instructions; and
    one or more processors configured to execute the programmed instructions stored in the memory, wherein the one or more processors when executing the programmed instructions perform the following operations:
        acquire ultrasound data along a first two-dimensional (2D) plane and a second 2D plane from the matrix array probe for a region of interest (ROI), wherein the first 2D plane is orthogonal to the second 2D plane;
        calculate a first flow velocity within the ROI based on the ultrasound data along the first 2D plane;
        calculate a second flow velocity within the ROI based on the ultrasound data along the second 2D plane;
        generate a color flow image based on the first flow velocity;
        generate a set of graphical indicators based on the second flow velocity;
        generate and display an anatomical image on a display, the anatomical image based on the ultrasound data acquired along the first 2D plane; and
        overlay the color flow image and the set of graphical indicators on the anatomical image on the display, wherein the set of graphical indicators are displayed as an animated repeating sequence that successively cycles between different graphical indicators in the set to represent the second flow velocity.

10. The ultrasound imaging system of claim 9, wherein the color flow image includes a color spectrum that represents the first flow velocity.

11. The ultrasound imaging system of claim 9, wherein the one or more processors are further configured to perform the following operations:
- determine an adjustment direction of the matrix array probe based on the second flow velocity, the adjustment direction corresponding to a change in tilt angle of the matrix array probe to enable alignment of the second flow velocity with one of the first 2D plane or the second 2D plane; and
- generate and display an indicator icon on the display, the indicator icon indicating the adjustment direction.

12. The ultrasound imaging system of claim 9, wherein the graphical indicators in the set have different sizes and are concentric.

13. The ultrasound imaging system of claim 9, wherein a rate at which the graphical indicators in the set are successively cycled represents a magnitude of the second flow velocity.

14. The ultrasound imaging system of claim 9, wherein an order at which the graphical indicators in the set are successively cycled represents a direction of the second flow velocity relative to the first 2D plane.

15. The ultrasound imaging system of claim 9, wherein the first flow velocity and the second flow velocity are measurements of blood flow through the ROI.

16. A tangible and non-transitory computer readable medium comprising one or more computer software modules configured to direct one or more processors to:
- acquire ultrasound data along a first two-dimensional (2D) plane and a second 2D plane from a matrix array probe for a region of interest (ROI), wherein the first 2D plane is orthogonal to the second 2D plane;
- calculate a first flow velocity within the ROI based on the ultrasound data along the first 2D plane;
- calculate a second flow velocity within the ROI based on the ultrasound data along the second 2D plane;
- generate a color flow image based on the first flow velocity;
- generate a set of graphical indicators based on the second flow velocity;
- generate and display an anatomical image on a display, the anatomical image based on the ultrasound data acquired along the first 2D plane; and
- overlay the color flow image and the set of graphical indicators on the anatomical image on the display, wherein the set of graphical indicators are displayed as an animated repeating sequence that successively cycles between different graphical indicators in the set to represent the second flow velocity.

17. The tangible and non-transitory computer readable medium of claim 16, wherein the color flow image includes a color spectrum that represents the first flow velocity.

18. The tangible and non-transitory computer readable medium of claim 16, wherein the one or more computer software modules are further configured to direct one or more processors to:
- determine an adjustment direction of the matrix array probe based on the second flow velocity, the adjustment direction corresponding to a change in tilt angle of the matrix array probe to enable alignment of the second flow velocity with one of the first 2D plane or the second 2D plane; and
- generate and display an indicator icon on the display, the indicator icon indicating the adjustment direction.

19. The tangible and non-transitory computer readable medium of claim 16, wherein a rate at which the graphical indicators in the set are successively cycled represents a magnitude of the second flow velocity.

20. The tangible and non-transitory computer readable medium of claim 16, wherein an order at which the graphical indicators in the set are successively cycled represents a direction of the second flow velocity relative to the first 2D plane.

* * * * *